United States Patent [19]

Artmann

[11] Patent Number: 4,567,750
[45] Date of Patent: Feb. 4, 1986

[54] PROCESS AND DEVICE FOR DETECTION AND/OR MEASURING OF THE PARTICLE CONTENT IN GASES

[75] Inventor: Joachim Artmann, Aidlingen, Fed. Rep. of Germany

[73] Assignee: Robert Bosch GmbH, Stuttgart, Fed. Rep. of Germany

[21] Appl. No.: 645,815

[22] PCT Filed: Jan. 21, 1984

[86] PCT No.: PCT/DE84/00016
§ 371 Date: Aug. 27, 1984
§ 102(e) Date: Aug. 27, 1984

[87] PCT Pub. No.: WO84/03148
PCT Pub. Date: Aug. 16, 1984

[30] Foreign Application Priority Data

Feb. 12, 1983 [DE] Fed. Rep. of Germany ....... 3304846

[51] Int. Cl.$^4$ ............................................. G01N 27/16
[52] U.S. Cl. .......................................... 73/28; 340/627
[58] Field of Search .......................... 73/23, 28, 27 R; 340/627; 123/440, 489; 422/68; 436/155

[56] References Cited

U.S. PATENT DOCUMENTS 2,702,471 2/1955 Vonnegut ................................. 73/28
3,986,386 10/1976 Beltzer et al. ........................... 73/28

FOREIGN PATENT DOCUMENTS 2706668 8/1978 Fed. Rep. of Germany .
2367285 5/1978 France .

Primary Examiner—Stephen A. Kreitman
Attorney, Agent, or Firm—Michael J. Striker

[57] ABSTRACT

Detecting or measuring of the particle content in gases particularly in exhaust gases of fossil fuels such as soot concentration in exhaust gas of diesel engine and the like, is performed by means of arranging in a gas flow of a sensor which has two electrically heating faces for particle deposition and arranged in two parallel bridge branches of a Wheatstone bridge circuit, wherein one of the heating faces is constantly preheated so that the particle deposition on its surface is at a minimum, voltage or current or their increase are measured in a diagonal branch of the bridge circuit during a heating time period, and a warning signal or a measuring value for the particle content is derived from a maximum of the voltage or current or from a steepness of the voltage or current increase.

17 Claims, 5 Drawing Figures

PROCESS AND DEVICE FOR DETECTION AND/OR MEASURING OF THE PARTICLE CONTENT IN GASES

BACKGROUND OF THE INVENTION

The invention relates to a process and a device for detection and/or measuring the particle content in gases, in particular in exhaust gases of fossil fuels, like the soot concentration in the exhaust gas of Diesel motors and the like, of the genus stated in the preamble of claim 1.

The degree of blackening of a soot filter being admitted by the exhaust gas is used and evaluated as the measurement for the soot concentration in a known process of this type for determining the soot concentration in exhaust gases of internal combustion engines or oil burning installations. However, it is a prerequisite of such a process that the filter is free from soot at the outset of the measuring process. The filter must then be either cleaned or replaced by a new filter after the measuring process. For cleaning purposes the filter is frequently heated thus burning off the soot layer.

The replacing as well as the cleaning of the filter is not only very cumbersome, but it also requires considerable installation time. Therefore, the known process is only used in the stationary operation, for example, for adjusting the motor at the motor manufacturing plant or in oil burning installations.

SUMMARY OF THE INVENTION

The object of the invention is to provide a process which the invention and in accordance with the characterizing is suitable to be used in the nonstationary operation, for example, in the vehicle itself.

In the process of the invention two electrical heating faces (11, 12) are provided as sensor and arranged in two parallel bridge branches of a Wheatstone bridge circuit, one heating face (11) is constantly so preheated that the particle deposition on its surface is at a minimum, the voltage or current, or the increase in voltage or current are measured in a diagonal branch of the Wheatstone bridge circuit during a heating time period, and a warning signal or a measuring value for the particle content is derived from the voltage or current maximum or the steepness of the voltage or current increase.

The process in accordance with the invention uses the fact that the removal of the particle deposition, like soot and the like, on the sensor is an endothermic process, that is, it consumes heat. Therefore. the heat energy which is required for heating the heating face for removing the particle deposition must be higher on a heating face which is covered with a particle deposition than with a clean surface. Therefore, in accordance with the process of the invention the hitherto additionally required cleaning procedure of the sensor is used for measuring the particle content. Due to this timely coupling of burning free the sensor and the measuring procedure, the total measuring time required is considerably shortened, in such a manner that one can obtain from the measuring a controller output for a constant control procedure for setting the engine. Measurements have shown that when using platinum coils as heating faces the normal voltage or current maximum in accordance with the invention is traversed in less than 50 ms. Therefore, the measuring procedure can be performed automatically and constantly with a small period cycle which provides the prerequisite for the nonstationary application of the process in the vehicle itself, for example, and also offers the possibility for controlling the motor setting.

The device of the invention includes two electrical heating faces (11, 12) provided as a sensor and arranged in two parallel bridge branch of a Wheatstone bridge circuit, one heating face is constantly so preheated that the particle deposition on its surface is at a minimum, means is provided for measuring the voltage or current, or the increase in voltage or current in a diagonal branch of the Wheatstone bridge circuit (17) during a heating time period, and means is provided for deriving signal or a measuring value for the particle content from the voltage or current maximum or the steepness of the voltage or current increase.

In accordance with advantageous embodiment of the device the Wheatstone bridge circuit is used with the two heat faces in parallel bridge branches by means of a selector switch in such a manner that in the one switch position only the heating face is operated with an appreciable heat filament energy consumption with which a surface temperature of more than 200° C. can be obtained and in the other switch position both heating faces are heated with full heat filament energy consumption, so that a surface temperature of more than 400° C. is obtained at both heating faces. The selector switch can be automatically actuated by means of a control device, whereby the one reverse switching moment is determined by an advance time and the other reverse switching moment is determined by the time interval until traversing the voltage or current maximum.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE EXEMPLIFIED EMBODIMENT

Figure 1:
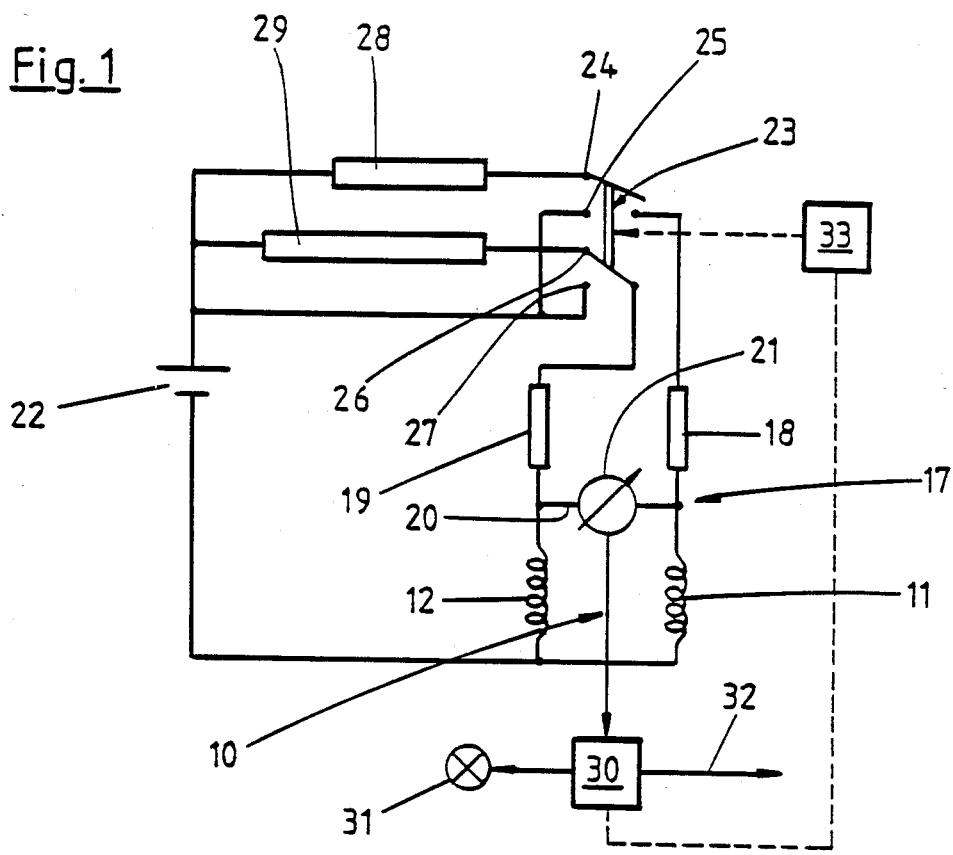
FIG. 1 an electrical circuit diagram of a device for detection and/or measuring the soot concentration in the exhaust gas of a Diesel engine, FIG. 2 a diagram of the chronological curve of the voltage or the current in the diagonal branch of the Wheatstone circuit in FIG. 1, FIG. 3 a schematic illustration of the arrangement of a sensor in FIG. 1 in the gas flow.
Figure 3:
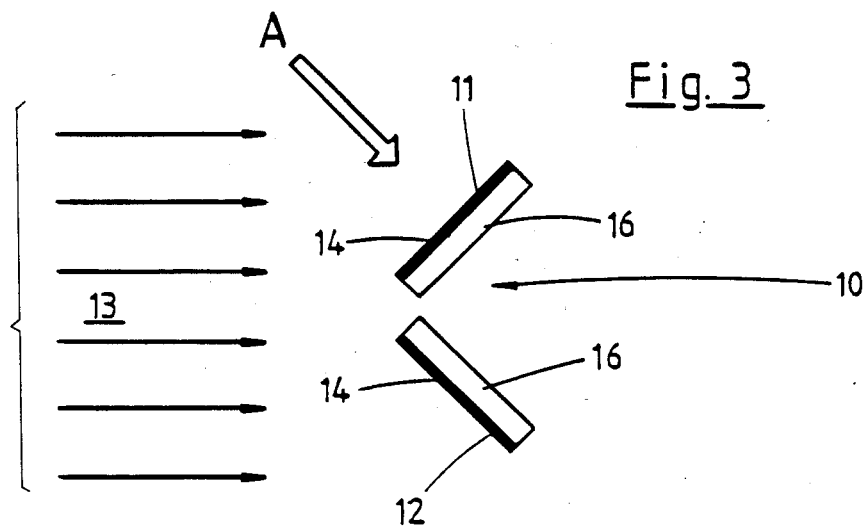
Figure 4:
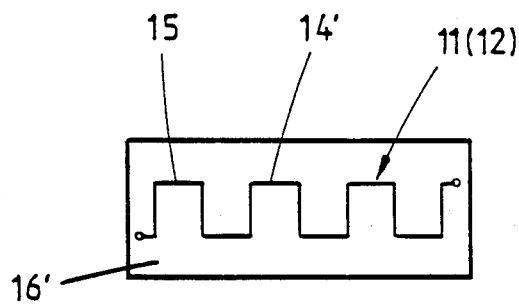
FIGS. 4 and 5 are plan views of a partial element of the sensor in the direction of arrow A in FIG. 3 in accordance with a first and a second exemplified embodiment.
Figure 5:
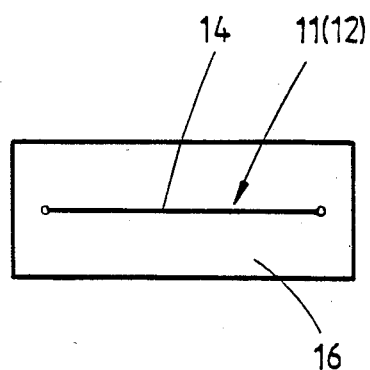

The device illustrated in a circuit diagram in FIG. 1 for the detection and/or measuring the soot concentration in the exhaust gas of Diesel engines is provided with a sensor 10 which is exposed to the exhaust gas. As can be seen from FIGS. 1 and 3, the sensor is provided with two heating faces 11 and 12 which are disposed in a wedge like manner and are so positioned in the gas flow 13 (FIG. 3) that their sweepbacks are directed opposite to the flow direction of the gas flow. Each heating face 11 or 12 is formed by a heating coil 14 or 14' made of platinum. It is formed elongated in the exemplified embodiment of FIG. 5 and is formed as a coil 15 in the exemplified embodiment of FIG. 4. The heating wire 14 or 14' is mounted on a ceramic substrate platelet 16 or 16' by means of a screen printing process, for example.

As can be seen from FIG. 1, the electrical heating faces 11,12 are disposed in parallel bridge branches of a Wheatstone bridge circuit 17. A measurement value receiver 21 is disposed in the diagonal branch 20 of the Wheatstone bridge circuit 17 and is either a voltage meter or a current meter. The two ends of the electrical heat faces 11,12 which are not connected with the resistors 18 or 19 are connected with the negative pole of a direct current source 22, while the two ends of the resistors 18,19 which are not connected with the heating surfaces 11,12 are connected with one of two outputs of a two pole reverse switch 23. The four inputs 24–27 of the two pole reverse switch 23 are connected with the positive pole of the direct voltage source 22. The first input 24 is connected with the positive pole at the direct voltage source 22 through a resistor 28, the second input is connected through a resistor 29 whose resistance value is higher than the one of the resistor 28, and the two other inputs 26 and 27 are provided for the other switch position of the reverse switch 23, are connected directly.

The measuring or detection process for the soot concentration in the exhaust gas is carried out with the aforementioned described device as follows:

At first, reverse switch 23 assumes the position illustrated in FIG. 1. In view of the aforementioned dimensioning of resistors 28 and 29 a heating current flows through the heating face 11 which causes a preheating of the heating face 11 to about 200°, so that no noticeable sooting occurs on the surface of heating face 11 in view of this heating. In contrast thereto, the heating face 12 does hardly receive a noticable heating current because of its very high resistor 29, whereby its temperature is not substantially increased or not increased at all.

Figure 2:
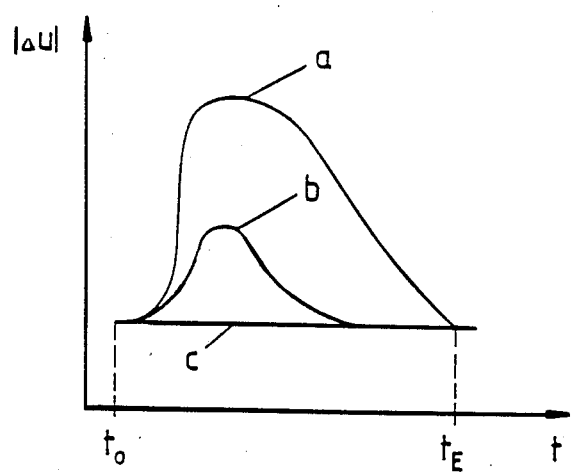

After a time interval, at which a minimum assumed soot deposition has precipitated on the substantially unheated and cold heating face 12, the reverse switch 23 is reversed and the two heating faces 11 and 12 are loaded with a full filament heat energy during a time period. During this heating time period, either the current which flows through the diagonal branch 20 of the Wheatstone bridge circuit 17 or the dropping voltage through diagonal branch 20 is measured. Arbitrary selected examples of the chronological voltage path 20 are shown in FIG. 2. The heating face 12 in the voltage path a was very much sooted during the time period of the reversal of reversal switch 23. During a lesser soot deposition on heating face 12 one receives the voltage path in accordance with curve b and when no soot is present on the heating face 12 one obtains a voltage path in accordance curve c. During the time period $t_o$, the reverse switch 23 is switched from its position shown in FIG. 1 into its other switch position. The starting point $t_o$ and the end point $t_E$ of curves a and b are on the t-axis during a uniform dimensioning of resistors 18 and 19. Also the curve c coincides with the t-axis. The filament heat energy of the two hot faces 11 and 12 is so selected that the surface temperature of both heating faces 11,12 reaches at least 400° during the heating time period. Thereby, the heat time period, that is, the time during which the two heat faces 11,12 are connected directly with the direct voltage source 22 through resistors 18 and 19 is so selected that at least the current or voltage maximum is obtained. The preswitched interval, which is preswitched before this heating time duration, is dimensioned so large that an assumed minimum soot deposition cannot form on the preheated heating face 12.

The measured value which had been received by the measuring value receiver 21, that is, the current or voltage path in accordance with FIG. 2, is fed to a signal processing device 30 which determines either the current or the voltage maximum of the chronological current or voltage increase and generates therefrom either a warning signal for an indicator 31 or a n output controller for controlling the engine setting which is fed through line 32 to a control circuit (not shown) for the engine setting. The illumination of indicator 31 signals the exceeding of an assumed maximum permissible soot concentration in the exhaust of the Diesel engine.

A control device 33 takes care of the automatic operation of the aforementioned described measuring procedure, whereby the signal processing device 30 of the control device 33 indicates the end of the measuring time period and the control device 33 defines the period duration until the repetition of the individual measuring operations, and also reverses the reverse switch 23 for initiating and finishing of a given measuring operation.

I claim:

1. A process of detecting and measuring the particle content in gases, particularly in exhaust gases of fossil fuels such as soot concentration in exhaust gas of Diesel engines and the like, comprising the steps of providing a sensor having two electrical heating faces to be positioned in a gas flow for deposition of particles thereon; arranging said two electrical heating faces in two parallel branches of a Wheatstone bridge circuit; preheating one of said heating faces so that the particle deposition on its surface is at a minimum; heating the heaating faces during a heating time period, measuring voltage or current or their increase in a diagonal branch of the Wheatstone bridge circuit during the heating time period; and deriving a warning signal or a measuring value for the particle from a maximum of the voltage or current or from a steepness of the voltage or current increase.

2. A process as defined in claim 1; and further comprising the step of the obtaining a controller output for an engine from the particle measuring value.

3. A process as defined in claim 1, wherein said heating step includes heating during such a time period which corresponds to at least to a time interval in which the voltage or curent maximum is obtained.

4. A process as defined in claim 1; and further comprising preswitching such a large preswitched interval to one given heating time period that a predetermined minimum particle deposition can form on the other non-preheated heating face.

5. A process as defined in claim 1, wherein said preheating step includes preheating the one heating face so that it reaches a surface temperature of more than 200° C.

6. A process as defined in claim 1, wherein said heating step includes dimensioning filament heat energy during the heating period so that a surface temperature of the two heating faces reaches at least 40° C.

7. A device for detecting and measuring the particle content in gases, particularly in exhaust gases of fossil fuels, such as soot concentration in exhaust gas of Diesel engines and the like, comprising a sensor including two electrical heating faces arranged to be positioned in a gas flow for particle deposition thereon; a Wheatstone bridge circuit having two parallel bridge branches and a diagonal branch, said two electrical heating faces being arranged in said parallel bridge branches of said Wheatstone bridge circuit; means for preheating one of said heating faces constantly so that particle deposition on its surface is at a minimum, and for heating said two electrical heating faces during a heating time period; means for measuring voltage for current or their increase in said diagonal branch of said Wheatstone bridge circuit during said heating time period; and means for deriving a warning signal or a measuring value for the particle content from a maximum of the voltage or current, or from a steepness of the voltage or current increase.

8. A device as defined in claim 7; and further comprising a first resistance with which said first heating face is connected in series in a first connecting point and a second resistance with which said second heating face is connected in series in a second connecting point, said second resistance is parallel to said first resistence, said measuring means being arranged between said two connecting points, said heating means icluding a direct voltage source and a two pole reverse switch having two outputs each connected with a respective one of said resistences and four imputs arranged so that a first input is connected with said direct voltage source through a third resistence, a second input is connected with said direct voltage source through a fourth resistence which is substantially larger than said third resistence, and a third and a fourth inputs are directly connected with said direct voltage source.

9. A device as defined in claim 8, wherein said measuring means is a voltage or current meter.

10. A device as defined in claim 9, wherein said deriving means includes a signal processing device which is connected with said voltage or current meter and generates a warning or control signal from the maximum of the voltage or current or from the voltage or current increase.

11. A device as defined in claim 7, wherein said electrical heating faces are arranged in a wedge-like manner and directed in the gas flow so that their sweepback is directed opposite to the flow direction.

12. A device as defined in claim 7, wherein said electrical heating faces are provided with a heating wire.

13. A device as defined in claim 12, wherein said heating wire is composed of platinum.

14. A device as defined in claim 12, wherein said heating wire is an elongated substantially straight wire.

15. A device as defined in claim 12, wherein said heating wire is formed as a coiled wire.

16. A device as defined in claim 12, wherein said electrical heating faces also have a ceramic substrate, said heating wire being mounted on said ceramic substrate.

17. A device as defined in claim 16, wherein said heating wire is formed as a screen-printed wire on said ceramic substrate.

* * * * *